(12) United States Patent
Altaf et al.

(10) Patent No.: US 10,688,224 B1
(45) Date of Patent: Jun. 23, 2020

(54) PROSTHETIC IMPLANTABLE ANTIBACTERIAL SURGICAL MESH

(71) Applicant: King Abdulaziz University, Jeddah (SA)

(72) Inventors: Abdulmalik Mohammed Saleh Altaf, Jeddah (SA); Seham Alsayed Abdulhady, Cairo (EG); Faissal Abdel-Hady, South-Windsor, CT (US); Mahmoud Abdul Megead Yassien, Cairo (EG)

(73) Assignee: King Abdulaziz University, Jeddah (SA)

(*) Notice: Subject to any disclaimer, the term of this patent is extended or adjusted under 35 U.S.C. 154(b) by 0 days.

(21) Appl. No.: 16/502,662

(22) Filed: Jul. 3, 2019

(51) Int. Cl.
| | |
|---|---|
| *A61L 31/04* | (2006.01) |
| *A61L 31/10* | (2006.01) |
| *A61K 31/47* | (2006.01) |
| *A61K 31/497* | (2006.01) |
| *D04H 1/728* | (2012.01) |
| *A61L 31/16* | (2006.01) |

(52) U.S. Cl.
CPC ............ *A61L 31/10* (2013.01); *A61K 31/47* (2013.01); *A61K 31/497* (2013.01); *A61L 31/16* (2013.01); *D04H 1/728* (2013.01); *A61L 2300/406* (2013.01); *A61L 2400/12* (2013.01); *A61L 2430/34* (2013.01)

(58) Field of Classification Search
None
See application file for complete search history.

(56) References Cited

U.S. PATENT DOCUMENTS

| | | | |
|---|---|---|---|
| 8,946,227 B2 | 2/2015 | Magar et al. | |
| 9,095,524 B2 | 8/2015 | Warnke et al. | |
| 2008/0097280 A1 | 4/2008 | Martin et al. | |
| 2009/0148486 A1 | 6/2009 | Lu et al. | |
| 2010/0047309 A1 | 2/2010 | Lu et al. | |
| 2013/0030452 A1* | 1/2013 | Itskovitz-Eldor | ....... A61L 27/34 606/151 |

FOREIGN PATENT DOCUMENTS

| | | |
|---|---|---|
| KR | 10-1362286 | 2/2014 |
| WO | 2014/074503 A1 | 5/2014 |

OTHER PUBLICATIONS

Yuan, Y.; Chesnutt, B. M.; Haggard, W. O.; Bumgardner, J. D. Deacetylation of Chitosan: Material Characterization and in vitro Evaluation via Albumin Adsorption and Pre-Osteoblastic Cell Cultures. Materials, 4, 1399-1416. (Year: 2011).*
Abbaspour, et al. ; Evaluation of the Antimicrobial Effect of Chitosan/Polyvinyl Alcohol Electrospun Nanofibers Containing Mafenide Acetate ; Jundishapur J Microbiol. 8(10) ; Oct. 2015 ; 6 Pages.
Zupancic, et al. ; Long-Term Sustained Ciprofloxacin Release from PMMA and Hydrophilic Polymer Blended Nanofibers ; Molecular Pharmaceutics 13(1) ; pp. 295-305 ; 2016 ; Abstract Only ; 2 Pages.
Moydeen, et al. ; Fabrication of electrospun poly(vinyl alcohol)/dextran nanofibers via emulsion process as drug delivery system: Kinetics and in vitro release study ; International Journal of Biological Macromolecules vol. 116 ; pp. 1250-1259 ; Sep. 2018 ; Abstract Only ; 2 Pages.
Springer ; Fabrication of chitosan microparticles loaded in chitosan and poly(vinyl alcohol) scaffolds for tissue engineering application ; Bulletin of Materials Science, vol. 40, Issue 4 ; pp. 645-653 ; Aug. 2017 ; Abstract Only ; 1 Page.
Sarhan, et al. ; Apitherapeutics and phage-loaded nanofiobers as wound dressing with enhanced wound healing and antibacterial activity ; Nanomedicine vol. 12, No. 17 ; Aug. 14, 2017 ; Abstract Only ; 1 Page.

* cited by examiner

*Primary Examiner* — Jessica Worsham
(74) *Attorney, Agent, or Firm* — Oblon, McClelland, Maier & Neustadt, L.L.P.

(57) ABSTRACT

The disclosed invention is directed to an implantable surgical prosthetic mesh having a nanofiber comprising one or more antibiotic and a polysaccharide, and a non-polysaccharide polymer deposited on the mesh. The mesh of the invention is shown to be effective in eliminating or minimizing the bacterial population in the mesh and surrounding tissue for at least 14 days from surgical implantation of the mesh.

17 Claims, 12 Drawing Sheets

PROSTHETIC IMPLANTABLE ANTIBACTERIAL SURGICAL MESH

BACKGROUND OF THE INVENTION

Field of the Disclosure

The present invention relates to an implantable surgical mesh having a nanofiber comprising one or more antibiotic deposited on the surface of the mesh.

Description of Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present disclosure.

A hernia is an abnormal protrusion of intra-abdominal tissue or organ through a defect in the abdominal wall. Currently, the only effective treatment of a hernia is surgical repair of the defect. The use of mesh in surgical repair of hernias has dramatically decreased the incidence of hernia recurrence. However, postoperative mesh infection is a major complication that is difficult to treat. In most cases, surgical removal of the implanted mesh becomes necessary to obviate the complication which may cause a subsequent hernia recurrence and surgical intervention. Therefore, mesh infection incurs physical, economic and psychological impact on the patient. The incidence of mesh infection is higher when a mesh is used in a contaminated surgical field, such as in cases of strangulated hernias. Mesh infection is thought to be caused by the postoperative growth of bacteria present in the surgical field at the time of mesh insertion. As a foreign body, the mesh is devoid of any blood supply and, thus, forms a favorable nest for bacterial proliferation.

Nanofibers produced by electrospinning have been shown to be an efficient drug delivery system providing sustained release of drugs [Elakkiya et al. (2012) "Fabrication of electrospun poly 1-lactide and curcumin loaded poly 1-lactide nanofibers for drug delivery" Fibers and Polymers, 13: 623-630]. They are capable of delivering medicines directly to internal tissues due to their physical characteristics that include large surface area and permeability combined with inter-connecting pore structure of the fibers leading to efficient drug release as well as their ease of fabrication [Khan et al. (2012) "Nanofibers—a new trending nano drug delivery systems" International Journal of Pharmaceutical Research & Analysis. 3: 47-55].

Electrospinning is a promising technique for producing nano-scale fibers, which are excellent candidates for various applications, e.g., as a wound dressing and delivery system [Li et al. (2004) "Electrospinning of nanofibers: reinventing the wheel" Advanced Materials 16: 1151-1170]. It is a relatively simple and adaptable process to produce nanofiber from a polymer solution or melt which was patented by Formhals in the 1930s (U.S. Pat. Nos. 1,975,504, 2,160,962, and 2,187,306—each incorporated herein by reference in their entirety). The method comprises applying a high voltage electrical field between the tip of a nozzle and a collector in order to generate sufficient electrostatic force to overcome the surface tension of a droplet of the polymer solution at the nozzle tip. When the surface tension is overcome, the hemispherical surface of the fluid at the tip of the nozzle stretches to form a conical shape known as the Taylor cone [Taylor, G. L. (1969) "Electrically driven jets" Proceedings of the RoyalSociety of London A 313: 453, incorporated herein by reference in its entirety]. Further increase of the electric field's strength will deform the Taylor cone until a jet stream is extruded from the cone's apex. During the process, and depending on the solution properties and operating conditions, the solvent evaporates as the jet moves toward the collector which decreases the jet radius and increases the polymer concentration and viscosity. When the solvent is fully evaporated, the jet stretching stops and results in producing fiber of highly reduced diameter which deposits on the grounded collector in the form of a random nonwoven structure. The process of the electrospinning is well described, see for example Huang et al. ["A review on polymer nanofibers by electrospinning and their applications in nanocomposites" Composites Science and Technology (2003) 63(15): 2223-2253; Kim et al. ["Polybenzimidazole nanofiber produced by electrospinning" Polymer Engineering and Science (1999)39 (5): 849-854]; Fang et al. "DNA fibers by electrospinning" Journal of Macromolecular Science (1997) 36 (2): 169-173]; and Doshi et al. ["Electrospinning process and applications of electrospun fibers" Journal of Electrostatics (1995). 35 (2-3): 151-160]—each incorporated herein by reference in their entirety. Nanofibers in the range of 10 to 1000 nm diameter can be achieved by choosing the appropriate parameters such as viscosity, concentration, applied voltage, distance between the two electrodes, and nozzle tip (needle) diameters. However, the instability, the whipping of the fiber, and bead formation remain important problems in the electrospinning process.

Abdel Hady [Abdel-Hady et al. "Experimental validation of upward electrospinning process" Nanotechnology, Vol. 2011, 14 pages, http://dx.doi.org/10.5402/2011/851317; and Abdel-Hady et al. In Proceedings of the Egyptian Engineers Association Conference, (2009) Al Riyadh, Saudi Arabia—each of which is incorporated herein by reference in its entirety] introduced the upward electrospinning method that overcomes some of the shortcoming of the previous methods. In the method, the fiber is produced on a jet directed upward. The combination of gravitational force and surface tension oppose against the electrostatic force thereby stretching the fiber.

Abbaspour et al. [Junsishshapur J. Microbiol. (2015) 8 (10): e24239] disclose a chitosan/polyvinyl alcohol and mafenide acetate nanofiber containing 10% and 30% by weight chitosan and 20 and 40% mafenide acetate. Also, they disclose that films of nanofibers with and without mafenide acetate prevent bacterial penetration, but films with mafenide acetate were more effective, in particular against *Pseudomonas aeruginosa* and *Staphylcoccus aureus*.

Zupanicic et al. [Mol. Pharmaceutics (2016) 13 (1), 295-305] examine the long-term sustained release of ciprofloxacin from nanofiber of hydrophobic polymer such as poly(methyl methylacrylate) (PMMA) and polycaprolactone (PLC) and a blend of hydrophobic and hydrophilic polymers such as polyvinyl alcohol (PVA), polyethylene oxide (PEO), and chitosan. PEO containing nanofiber mats display high burst of drug release. In contrast, nanofiber containing PVA and chitosan show much small burst. In addition, the reference discloses that the release of the drug can be tuned by various blends of PMMA with PVA or chitosan.

Moydeen et al. [Int. J. Biol. Macromol. (2018) 116, 1250-1259] disclose the fabrication of electrospun polyvinyl alcohol/dextran as a carrier of drugs such as ciproflaxin. Also, they examine the release of the ciprofloxacin from the nanofiber and show that the core-shell nanofibers can sustain the ciprofloxacin release compared with the blending electrospinning nanofiber.

Murthy et al. [Bull. Mate. Sci. (2017) 40 (4) 645-653] disclose ciprofloxacin-loaded chitosan microparticles (CMP) impregnated in chitosan and poly(vinyl alcohol) (PVA) scaffold for effective delivery of drug in a sustained manner to wound site.

Such conventional drug-impregnated materials are not, however, effective for use in surgical treatment of hernias. Conventional materials are unable to provide drug release profiles that provide a steady and predictable threshold dosage of active material. In addition conventional materials do not exhibit good compatibility with live tissue to promote quick and lasting wound healing, especially for hernia surgery which occurs at a location on a human subject that is exposed to significant pressure and pulling strain.

Accordingly one object of the present disclosure is to provide an implantable surgical prosthesis mesh having nanofiber comprising a polysaccharide, one or more antibiotics, and a biocompatible polymer deposited on the surface of the mesh. The mesh of the invention provides continues source of antibiotics for more than 14 days to tissue after surgical implantation.

The foregoing paragraphs have been provided by way of general introduction, and are not intended to limit the scope of the following claims. The described embodiments, together with further advantages, will be best understood by reference to the following detailed description taken in conjunction with the accompanying drawings.

SUMMARY

A first aspect of the invention is directed to an implantable medical prosthetic mesh having nanofibers deposited on the surface of a mesh substrate, wherein the nanofibers comprise a polysaccharide, an antibiotic, and a biocompatible polymer.

In a preferred embodiment, the average diameter of the fiber is in the range of 50 nm to 300 nm and the bore size in the range of 300 nm to 900 nm.

In another preferred embodiment, the polysaccharide is chitosan, dextran, cellulose, or combination thereof.

In a more preferred embodiment, the polysaccharide is chitosan.

In another preferred embodiment, the chitosan has a degree of deacetylation in the range of 70% to 95%.

In another preferred embodiment, the antibiotic is a penicillin, tetracycline, cephalosporin, quinolone, lincomycin, macrolide, sulfonamide, glycopeptide, aminoglycoside, carbapenem, or combination thereof.

In a preferred embodiment, the antibiotic is a quinolone antibiotic.

In a preferred embodiment, the antibiotic is selected from the group consisting of lomefloxacine, ofloxacin, gatifloxacin, norfloxacin, ciprofloxacin, moxifloxacin, levofloxacin, gemifloxacin, delafloxacin, cinoxacin, nalidixic acid, trovafloxacin, sparfloxacin, and combinations thereof.

In a particularly preferred embodiment, the antibiotic is ciprofloxacin.

In another preferred embodiment, the polymer is selected from the group consisting of polyvinylalcohol, polyvinylpyralidone, poly(methacrylate) and polycaprolactone.

In another preferred embodiment, the mesh substrate comprises polypropylene, polytetrafluroethylene, polyethylene terephthalate, or polyvinylidene fluoride.

In another preferred embodiment, the mesh substrate comprises a biodegradable polymer.

In another preferred embodiment, the mesh is a polyester, polysaccharide, or polyurethane.

In another preferred embodiment, the mesh is a hernia mesh or pelvic mesh.

In another preferred embodiment, the polysaccharide is chitosan, the antibiotic is ciprofloxacin, and the polymer is polyvinyl alcohol or polyvinylpyrrolidone.

A second aspect of the invention is directed to a method of making an implantable medical prosthetic mesh comprising:

mixing a first solution containing a polysaccharide with a second solution comprising an antibiotic and a polymer, and electrospinning the solution mixture to nanofibers.

In a preferred embodiment, the ratio of the first solution/the second solution is in the range of 1 to 5.

In another preferred embodiment, the polysaccharide is chitosan.

In another preferred embodiment, the antibiotic is ciprofloxacin.

In another preferred embodiment, the polymer is polyvinyl alcohol, polyvinylpyrrolidone, or a mixture thereof.

In another preferred embodiment, the electrospinning is carried out by the upward electrospinning method.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION

Figure 1:
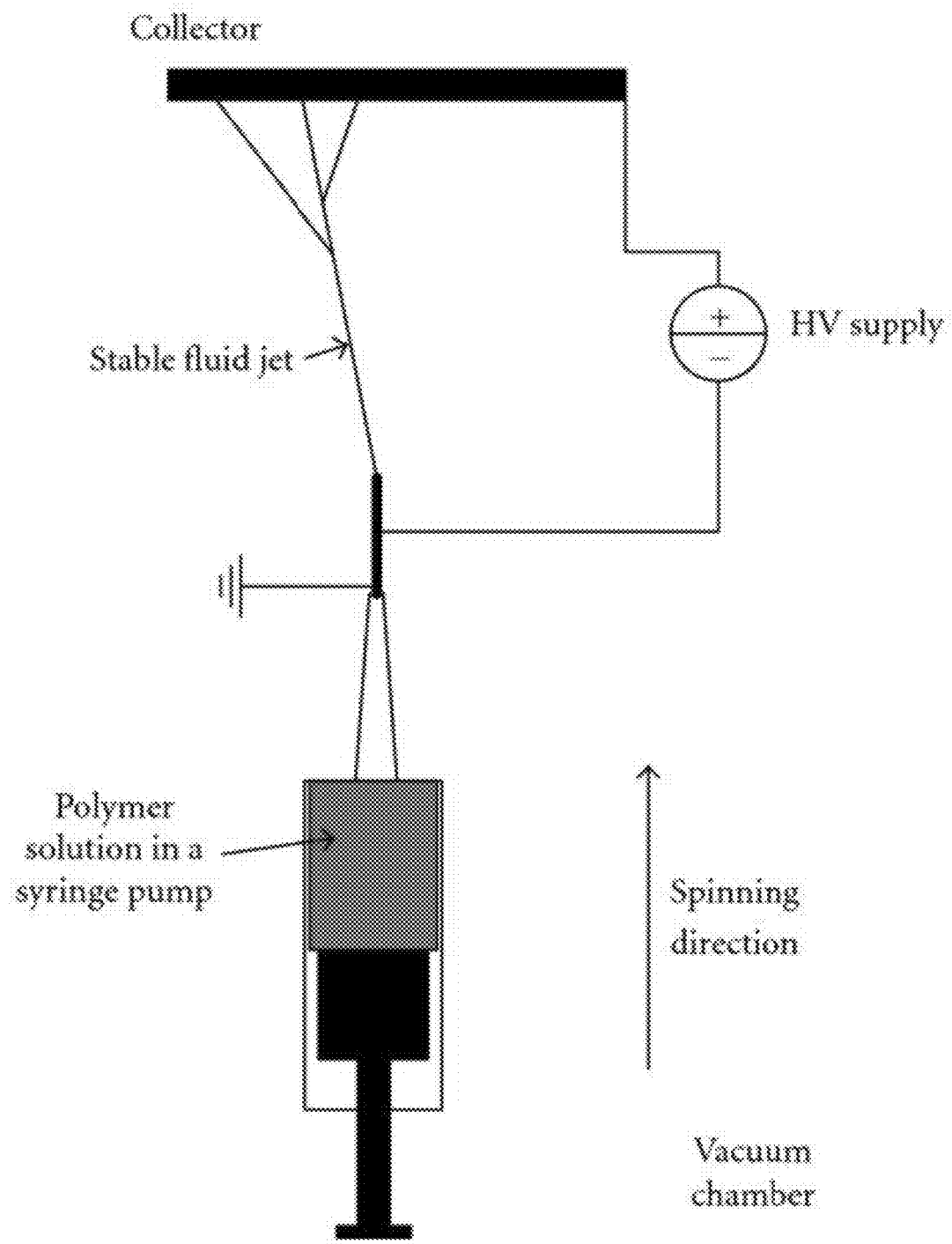
FIG. 1 shows a diagram of the upward electrospinning set up.

Embodiments of the present disclosure will now be described more fully hereinafter with reference to the accompanying drawings, in which some, but not all embodiments of the disclosure are shown. The present disclosure will be better understood with reference to the following definitions.

All publications mentioned herein are incorporated herein by reference in full for the purpose of describing and disclosing the methodologies, which are described in the publications, which might be used in connection with the description herein. Nothing herein is to be construed as an admission that the inventors are not entitled to antedate such disclosure by virtue of prior disclosure. Also, the use of "or" means "and/or" unless stated otherwise. Similarly, "comprise," "comprises," "comprising" "include," "includes," and "including" are interchangeable and not intended to be limiting.

As used herein, the term "compound" is intended to refer to a chemical entity, whether in a solid, liquid or gaseous phase, and whether in a crude mixture or purified and isolated.

As used herein, the term "salt" refers to derivatives of the disclosed compounds, monomers or polymers wherein the parent compound is modified by making acid or base salts thereof. Exemplary salts include, but are not limited to, mineral or organic acid salts of basic groups such as amines, and alkali or organic salts of acidic groups such as carboxylic acids. The salts of the present disclosure can be synthesized from the parent compound that contains a basic or acidic moiety by conventional chemical methods. Generally such salts can be prepared by reacting the free acid or base forms of these compounds with a stoichiometric amount of the appropriate base or acid in water or in an organic solvent, or in a mixture of the two; generally non-aqueous media like ether, ethyl acetate, ethanol, isopropanol, or acetonitrile are preferred.

As used herein, the term "about" refers to an approximate number within 20% of a stated value, preferably within 15% of a stated value, more preferably within 10% of a stated value, and most preferably within 5% of a stated value. For example, if a stated value is about 8.0, the value may vary in the range of 8±1.6, ±1.0, ±0.8, ±0.5, ±0.4, ±0.3, ±0.2, or ±0.1.

As used herein a "polymer" or "polymeric resin" refers to a large molecule or macromolecule, of many repeating subunits and/or substances composed of macromolecules. As used herein a "monomer" refers to a molecule or compound that may bind chemically to other molecules to form a polymer. As used herein the term "repeat unit" or "repeating unit" refers to a part of the polymer or resin whose repetition would produce the complete polymer chain (excluding the end groups) by linking the repeating units together successively along the chain. The method by which monomers combine end to end to form a polymer is referred to herein as "polymerization" or "polycondensation", monomers are molecules which can undergo polymerization, thereby contributing constitutional repeating units to the structures of a macromolecule or polymer. As used herein "resin" or "polymeric resin" refers to a solid or highly viscous substance or polymeric macromolecule containing polymers, preferably with reactive groups. As used herein a "copolymer" refers to a polymer derived from more than one species of monomer and are obtained by "copolymerization" of more than one species of monomer. Copolymers obtained by copolymerization of two monomer species may be termed bipolymers, those obtained from three monomers may be termed terpolymers and those obtained from four monomers may be termed quarterpolymers, etc. As used herein, "cross-linking", "cross-linked" or a "cross-link" refers to polymers and resins containing branches that connect polymer chains via bonds that link one polymer chain to another. The polymer may be natural or synthetic. Natural polymer includes, but not limited to polysaccharides such as, but not limited to cellulose, dextran, and natural polyesters. Synthetic polymers include but not limited to polypropylene, polyvinylalcohol, polyvinylpyralidone, polytetrafluroethylene, polyethylene terephthalate, and polyvinylidene fluoride.

A first aspect of the invention is directed to an implantable medical prosthetic mesh having nanofibers deposited on the surface of a mesh substrate, wherein the nanofibers comprise:

a polysaccharide in an amount in the range of 8 wt. % to 35 wt. %, an antibiotic in an amount in the range of 15 wt. % to 35 wt. %, and a polymer in an amount in the range of 45 wt. % to 70 wt. %.

Surgical mesh is a loosely woven or knitted sheet which is used as a permanent or temporary support for organs and other tissues during surgery. Surgical mesh is created from both inorganic and biological materials and is used in a variety of surgeries. Permanent meshes remain in the body, whereas temporary ones dissolve over time.

In some embodiments, yarns include at least two filaments which may be arranged to create openings there between, the yarns also being arranged relative to each other to form openings in the mesh. Alternatively, the mesh may be formed from a continuous yarn that is arranged in loops that give rise to the openings in the mesh. The use of a mesh having yarns spaced apart in accordance with the present disclosure has the advantage of reducing the foreign body mass that is implanted in the body, while maintaining sufficient tensile strength to securely support the defect and tissue being repaired by the mesh. Moreover, the openings of the mesh of the present disclosure may be sized to permit fibroblast through-growth and ordered collagen laydown, resulting in integration of the mesh into the body. Thus, the spacing between the yarns may vary depending on the surgical application and desired implant characteristics as envisioned by those skilled in the art. Moreover, due to the variety of sizes of defects, and of the various fascia that may need repair, the mesh may be of any suitable size.

In embodiments in which at least two filaments form a yarn, the filaments may be drawn, oriented, crinkled, twisted, braided, commingled or air entangled to form the yarn. The resulting yarns may be braided, twisted, aligned, fused, or otherwise joined to form a variety of different mesh shapes. The yarns may be woven, knitted, interlaced, braided, or formed into a surgical mesh by non-woven techniques. The structure of the mesh will vary depending upon the assembling technique utilized to form the mesh, as well as other factors, such as the type of fibers used, the tension at which the yarns are held, and the mechanical properties required of the mesh.

In some embodiments, knitting may be utilized to form a mesh of the present disclosure. Knitting involves, in embodiments, the intermeshing of yarns to form loops or inter-looping of the yarns. In embodiments, yarns may be warp-knitted thereby creating vertical interlocking loop chains, and/or yarns may be weft-knitted thereby creating rows of interlocking loop stitches across the mesh. In other embodiments, weaving may be utilized to form a mesh of the present disclosure. Weaving may include, in embodiments, the intersection of two sets of straight yarns, warp and weft, which cross and interweave at right angles to each other, or the interlacing of two yarns at right angles to each other. In some embodiments, the yarns may be arranged to form a net mesh which has isotropic or near isotropic tensile strength and elasticity.

In some embodiments, the yarns may be nonwoven and formed by mechanically, chemically, or thermally bonding the yarns into a sheet or web in a random or systematic arrangement. For example, yarns may be mechanically bound by entangling the yarns to form the mesh by means other than knitting or weaving, such as matting, pressing, stitch-bonding, needlepunching, or otherwise interlocking the yarns to form a binderless network. In other embodiments, the yarns of the mesh may be chemically bound by use of an adhesive such as a hot melt adhesive, or thermally bound by applying a binder such as a powder, paste, or melt, and melting the binder on the sheet or web of yarns.

The mesh may be a composite of layers, including a fibrous layer as described above, as well as porous and/or non-porous layers of fibers, foams, and/or films. A non-porous layer may retard or prevent tissue ingrowth from surrounding tissues, thereby acting as an adhesion barrier and preventing the formation of unwanted scar tissue. In embodiments, a reinforcement member may be included in the composite mesh. Suitable meshes, for example, include a collagen composite mesh such as PARIETEX™ (Tyco Healthcare Group LP, d/b/a Covidien, North Haven, Conn.). PARIETEX™ composite mesh is a 3-dimensional polyester weave with a resorbable collagen film bonded on one side. Examples of other meshes which may be utilized include those disclosed in U.S. Pat. Nos. 6,596,002; 6,408,656; 7,021,086; 6,971,252; 6,695,855; 6,451,032; 6,443,964; 6,478,727; 6,391,060; and U.S. Patent Application Publication No. 2007/0032805, the entire disclosures of each of which are incorporated by reference herein.

The primary function of surgical mesh is to support prolapsed organs either temporarily or permanently. It is most commonly used in hernia surgery within the abdomen, which is required when an organ protrudes through abdominal muscles. Also, surgical mesh may be used for pelvic or vaginal wall reconstructions in women and is implemented to act as a growth guide for damaged tissue. Ideally, these implants should be strong enough to survive mechanical loads and actions of whichever body area they become a part of.

Mesh implantation is accompanied by a physiological response to the inserted mesh. A mesh constructed from biocompatible material would produce desired minimal response such as formation of fibrosis around the prosthesis, i.e., scar tissue formation. In some cases, an acute inflammatory reaction may be triggered due to the formation of giant cells and subsequently granulomas indicating that the tissue is "tolerating" the mesh material. In some other cases, a severe inflammatory response is developed during the integration of the mesh into the tissue leading to fibroblastic cell proliferation. Ultimately, the goal for surgical mesh development is to formulate one that has a minimal in vivo reaction to maximize comfort for the patient, avoid infection, and ensure smooth integration into the body for tissue with minimal response of the body to a foreign object.

A number of factors are involved in mesh biocompatibility. Mesh porosity is the ratio of pore to total area that plays a role in the development of bacterial infection or smooth tissue regeneration. Pore sizes below 10 μm are susceptible to infection because bacteria may enter and proliferate, whereas macrophages and neutrophils are too large to pass through and aid in fighting the bacteria. At pore sizes larger than 75 μm, fibroblasts, blood vessels, and collagen fibers infiltrate the mesh as part of tissue regeneration. Although there is no general consensus on the best pore size, it can be deduced that larger pores are better for development of tissue and integration in vivo.

Any biocompatible polymer may be utilized in formation of a mesh substrate of the invention. The selected polymer for the mesh substrate for the invention is dependent on the intended use of the mesh. The polymer can be selected from a wide array of natural and synthetic biocompatible polymers that include but is not limited to polypropylene, polyethylene terephthalate, polytetrafluroethylene polyvinylidene fluoride (PVDF), polylactic acid, polyglycolic acid, cellulose, dextrose, or combination thereof. In particular, PVDF mesh is resistant to hydrolysis and sufficiently flexible. Its use is described for both hernia and pelvic/vaginal wall surgery and is produced via fiber placement layer by layer.

Synthetic meshes are grouped as heavyweight or lightweight. The weight of the mesh depends on both the weight of the polymer and the amount of material used. Heavyweight meshes use thick polymers, have small pore size and high tensile strength. The weigh typically about 100 g/cm$^2$ (1.5 g for 10×15 cm mesh). In contrast, lightweight meshes are composed of thinner filaments with relatively large pores (>1 mm), and weigh typically about 33 g/cm$^2$ (0.5 g for 10×15 cm mesh). They contain less material, initiate less pronounced foreign body reaction, and are more elastic.

A deterioration of the tensile strength of the mesh or an increase in the ability of the mesh material to stretch could potentially lead to hernia recurrence or a poor functional result. Therefore, mesh materials must also possess the biomechanical properties necessary to withstand the stresses placed on the abdominal wall. This means that once the surgical mesh is implanted, some of the flexibility of the abdominal wall should be preserved. The natural elasticity of abdominal wall at 32 N/cm is about 38%. Lightweight meshes have an elasticity of about 20-35% at 16 N/cm, whereas heavyweight meshes have half of this elasticity (4-15% at 16 N/cm), and can restrict abdominal distension. Therefore, choosing a stronger mesh prosthetic should proceed cautiously. On the other hand, strain values greater than 30% indicate that these materials may stretch more than the native human abdominal wall, so may not maintain a functional repair and could result in bulging or recurrence.

Strength depends on filament type (multi- or mono-), woven or knitted, and the polymer type. Knitted meshes have greater flexibility and larger pores, but are not as strong compared to woven meshes. Knitted meshes can be stretched in any direction, whereas woven meshes allow stretching only in the direction oblique to the ninety degree intersection of the their strands. Orientation of the mesh also affects physico-mechanical properties during implantation. Therefore, meshes with anisotropic stretchability should be orientated with the most stretchable axis in the direction of least overlap to prevent early mesh dislocation.

The maximum intra-abdominal pressure generated in healthy adults occurs during jumping, and estimated to be about 170 mmHg. Meshes used to repair large hernias need to withstand at least 180 mmHg before bursting. All synthetic meshes are sufficiently strong. Most commonly used mesh prosthetics have a tensile strength of at least 32 N/cm. This is easily achieved as even the lightest meshes will withstand twice this pressure without bursting (burst pressure of Vypro 360 mmHg). This means that the tensile strengths of more than 100 N/cm of conventional heavyweight meshes (e.g. Prolene) are disproportional and not necessary for an effective repair. Therefore, mesh hernia repair failure often results from the separation of the mesh-fascia interface; not the mesh failing.

Composite meshes combine more than one material. The main advantage of a composite mesh is that it can be used in the intraperitoneal space with minimal adhesion formation. They require a specific orientation: the visceral side has a micro porous surface to prevent visceral adhesions, whereas the non-visceral side is often macro porous to allow parietal tissue ingrowth. The meshes are preferably one or other of polypropylene, polyester, and polytetrafluoroethylene, which are used in combination with each other or with additional materials such as titanium, omega 3, monocryl, polyvinylidene fluoride (PVDF) and hyaluronate.

There are two categories of composite meshes: absorbable and permanent. Barrier coatings in absorbable composite meshes require hydration prior to usage, and they are not amenable to modification, so they cannot be cut. However, they allow for neoepithelialization of the mesh before visceral adhesion, which mitigates viscera-mesh related complications, and can aid in tissue ingrowth. Parietex® composite mesh was the first to offer a resorbable collagen barrier on one side to limit visceral attachments and a three-dimensional polyester knit structure on the other to promote tissue ingrowth and ease of use. The collagen film is composed of glycerol, polyethylene glycol, and porcine collagen. This balance of material properties produces superior cellular proliferation when compared to polypropylene mesh in vitro and works with the body's natural systems to provide rapid fibrous ingrowth, minimal shrinkage, and strong tissue integration.

Permanently combined meshes take advantage of the properties of both macro and micro porous meshes. A micro porous mesh permits placement adjacent to viscera, whereas macro porous mesh promotes parietal tissue ingrowth. These meshes can be modified and are easily cut to fit specific applications. These properties permit intraperitoneal placement (e.g. Dual Mesh®, Dulex®, and Composix®).

Since the intended use of a mesh is to repair and support organs due to defects, the mesh may be configured to any suitable shape or size that is conducive to facilitating the correction or repair of the particular defect. The prosthetic mesh of the present invention may be manufactured by conventional techniques. For example the mesh may be cut into an appropriate shape by a cutting blade, hot knife, or ultrasonic cutting device to any size or shape appropriate for the intended use. The three dimensional structure of the device can be formed by shaping a sheet of mesh over a heated tool and cooling the sheet material to set the shape. In the case of biocompatible synthetic polymers such as but not limited to polypropylene knitted mesh, the mesh may be thermoformed over a heated tool in the range of from about 80° C. to about 160° C. and preferably about 118° C. under suitable pressure for a suitable amount of time in the range of 30 s to 30 min. The thermoforming should be conducted in a manner that does not distort or weaken the mesh structure. Generally polypropylene mesh should be compressed between a male and female forming tool which are closed together at a speed in the range of from about 2 to about 25 cm/min and preferable at a speed of in the range of from about 5 to about 7.5 cm/min. Polypropylene meshes should generally be heated for in the range of from about 2 to about 5 min and cooled to below room temperature to set the shape. Currently, it is preferred to cool polypropylene mesh to about 12° C. or less for a time in the range of 2 to about 5 min.

Several natural polysaccharides may be used to make the nanofibers to be deposited on the mesh of the invention. They include, but are not limited to hemicelluloses, cellulose, chitosan, and pectin. A single polysaccharide in the nanofibers or a combination of polysaccharide may be used in the nanofiber. Since polysaccharides biodegrade over time, the selection of the polysaccharide may affect the rate of release of the antibiotic from the mesh of the invention. In a preferred embodiment, the polysaccharide used in the nanofiber is chitosan. The amount of the polysaccharide constituent of the nanofiber is in the range of 2 wt. % to 55 wt. %, preferably in the range of 4 wt. % to 45 wt. %, more preferably 6 wt. % to 40, and most preferably in the range of 8 wt. % to 35 wt. % of the total weight of the nanofibers. In a particularly preferred embodiment, the polysaccharide is present in an amount in the range of 10 wt. % to 26 wt. % of the total weight of the nanofibers.

As used herein, chitosan is intended to refer to a chitin-derived polymer that is at least 50% deacetylated, preferably at least 70% deacylated, more preferably at 80% deacetylated, and most preferably at least 85% deacetylated. It is a linear polysaccharide composed of randomly distributed $\beta$-(1-4)-2-amino-2-D-glucosamine and $\beta$-(1-4)-2-acet-amido-2-D-glucoseamine (acetylated) units, and derived from chitin, a naturally occurring polymer. Chitin is a white, hard, inelastic, nitrogenous polysaccharide isolated from fungi, mollusks, or from the exoskeletons of arthropods such as crustaceans and insects. The major procedure for obtaining chitosan is the alkaline deacetylation of chitin with strong alkaline solution. Generally, the raw material is crushed, washed with water or detergent, and ground into small pieces. After grinding, the raw material is treated with alkali and acid to isolate the polymer from the raw crushed material. The polymer is then deacetylated by treatment with alkali. Chitin and chitosan differ in their degrees of deacetylation (DDA). Chitin has a degree of deacetylation of 0%, whereas pure chitosan has a degree of deacetylation of 100%. Typically, when the degree of deacetylation is greater than about 50% the polymer is referred to as chitosan. Chitosan is a cationic weak base that is substantially insoluble in water and organic solvents. Typically, chitosan is fairly soluble in dilute acid solutions, such as acetic, citric, oxalic, propionic, ascorbic, hydrochloric, formic, and lactic acids, as well as other organic and inorganic acids. Chitosan's charge gives it bioadhesive properties that allow it to bind to negatively charged surfaces, such as biological tissues present at a site of trauma or negatively charged implanted devices. Chitosan's degree of deacetylation affects it resorption. Chitosan compositions having a 50% degree of deacetylation are highly degradable in vivo. As the degree of deacetylation increases, chitosan becomes increasingly resistant to degradation. Chitosan compositions having a degree of deacetylation that is higher than 95% degrade slowly over weeks or months. In the body chitosan is degraded by lysozyme, N-acetyl-O-glucosaminidase and lipases. Lysozyme degrades chitosan by cleaving the glycosidic bonds between the repeating polysaccharide units. The byproducts of chitosan degradation are oligosaccharides and glucosamine that are gradually absorbed by the human body.

Therefore, when chitosan is used for the local delivery of therapeutic or prophylactic agents, no secondary removal operation is required.

The chitosan used in the nanofibers to be deposited on the implantable surgical mesh has a degree of deacetylation in the range of 50% to 95%, preferably in the range of 60% to 90%, more preferably in the range of 75% to 85% and most preferably about 85%. In some embodiment, the chitosan used has a uniform degree of deacylation. As used herein, the term "uniform degree of deacetylation" refers to a chitosan composition made from a single type of chitosan such as, but not limited to 61DDA, 71DDA, or 81DDA. Thus, a composition having a uniform degree of deacetylation excludes chitosan compositions having chitosans having different degrees of deacetylation. In some other embodiments, it may be desirable to use a composition comprising a mixture chitosan of preparation having different degrees of deacetylation.

There are many antibiotics known in the art of which one or more may be incorporated into the nanofibers. Some of the antibiotics display a broad spectrum bactericidal activity; whereas others have a narrow spectrum of bactericidal activity. In some locations such as hospitals, antibiotic resistant strains may be developed due to common use of a specific antibiotics or class of antibiotics. In such a case, a cocktail of antibiotics from one or more classes of antibiotics may be used in the nanofibers. The amount of the total antibiotic in the nanofiber is in the range of 5 wt. % to 55 wt. %, preferably in the range of 10 wt. % to 45 wt. %, more preferably 15 wt. % to 40, and most preferably in the range of 20 wt. % to 30 wt. % of the total weight of the nanofibers. In a particularly preferred embodiment, the total antibiotic is in an amount in the range of 20 wt. % to 25 wt. % of the total weight of the nanofibers. The antibiotics are divided into ten classes:

(1) Penicillins including but not limited to, Amoxicillin, Ampicillin, Carbenicillin, Piperacillin, Ticarcillin, Penicillin g benzathine, Procaine penicillin, and Penicillin v potassium, Oxacillin, Dicloxacillin, and Nafcillin. Since beta-lactamase is an enzyme which many bacteria acquire to become resistant to penicillin, a beta-lactmase inhibitor may be used with some of the penicillins to obviate antibiotic resistance, in particular, with penicillins such as clavulanate, sulbactam, and tazobactam.

(2) Tetracyclines including, but not limited to, Tetracycline, Doxycycline, Demeclocycline, Minocycline, Oxytetracycline, Omadacycline, Sarecycline, and Eravacycline (3) Cephalosporins including, but not limited to, Cefadroxil, Cephradine, Cefazolin, Cefazolin, Cephalexin, Cefepime, Ceftaroline, Cefoxitin, Loracarbef, Cefprozil, Cefuroxime, Cefotetan, Loracabef, Ceftibuten, Ceftriaxone, Cefotamime, Cefdinir, Cefixime, Cefdinir, Cefditoren, and Ceftazidime, (4) Quinolones including, but not limited to, Lomefloxacine, Ofloxacin, Gatifloxacin, Norfloxacin, Ciprofloxacin, Moxifloxacin, Levofloxacin, Gemifloxacin, Delafloxacin, Cinoxacin, Nalidixic acid, Trovafloxacin, and Sparfloxacin.

(5) Lincomycins including, but not limited to, Lincomycin and Clindamycin.

(6) Macrolides include, but not limited to, Telithromycin, Erythromycin, Azithromycin, Clarithromycin, and Fidaxomicin.

(7) Sulfonamides including, but not limited to, Sulfisoxazole and Sulfamethoxazole.

(8) Glycopeptides including, but not limited to, Vancomycin, Oritavancin, and Telavancin (9) Aminoglycosides including, but not limited to, Paromomycin, Tobramycin, Gentamicin, Amikacin, Kanamycin, Neomycin, and Plazomycin.

(10) Carbapenems including, but not limited to, Ertapenem, Cilastatin, and Imipenem.

In some preferred embodiments, quinolone antibiotics are preferably incorporated alone or in combination with other antibiotics because of their broad spectrum bactericidal activity. In a particular preferred embodiment, ciprofloxacin or salt thereof is used as the antibiotic used in the nanofibers deposited on the surgical mesh.

The polymer of the nanofiber may be the same or different from that of the mesh substrate. It can be natural or synthetic as long as it is a biocompatible polymer. Natural biocompatible polymers include, but are not limited to, polysaccharides such as, but not limited to cellulose, hemicellulose, pectin, dextran, and natural polyesters such as, but not limited to, polyglycolic acid or polylactic acid. Synthetic polymers include but not limited to polypropylene, polyurethane, polycarbonate, polyvinyl chloride, poly(methyl methacrylate), polyvinylalcohol, polyvinylfluoride, polyvinylpyrrolidone, polytetrafluroethylene, polyethylene terephthalate, polyvinyledene fluoride, and the like. In some embodiments, it may be desirable to use one polymers having desired characteristics, whereas in other embodiments an engineered blend of polymer may be used to obtain the desired characteristics. The amount of the total polymer in the nanofiber is at least 20 wt. %, preferably at least 30 wt. %, more preferably at least 40 wt. %, and most preferably at least 50 wt. % of the total weight of the nanofibers. In a particularly preferred embodiment, the total antibiotic is in an amount in the range of 50 wt. % to 60 wt. % of the total weight of the nanofibers.

The nanofibers deposited on the mesh substrate have an average diameter in the range of 5 nm to 900 nm, preferably in the range of 15 nm to 700 nm, more preferably in the range of 30 nm to 550 nm, even more preferably in the range of 40 nm to 400 nm, and most preferably in the range of 50 nm to 300 nm. Also, they have a bore size in the range of 50 nm to 1000 nm, preferably in the range 200 nm to 900 nm, more preferably in the range of 300 nm to 800 nm, and most preferably in the range of 500 nm to 700 nm. The amount of the nanofibers deposited on the mesh is in the range of 1.0 wt % to 30 wt %, preferably in the range of 5 wt % to 20 wt %, preferably 10 wt. % to 15 wt % of the total weight of the mesh and the nanofibers.

The nanofiber deposited on the implantable surgical mesh functions as a long term antibiotic release system. As used herein, the term "long term antibiotic release" means that the antibiotic is eluted steadily from the fiber in a time frame in the range of one day to thirty days, preferably in the range of 5 days to 25 days, more preferably in the range 10 days to 20 days, and most preferably in the range of 13 days to 16 days. In a particularly preferred embodiment, the antibiotic is released from the fiber steadily for at least 14 days. Generally, the polymer has a drug release rate in the range of about 0.001 $\mu g/cm^2$ min to about 100 $\mu g/cm^2$ min, preferably in the range of about 0.01 $\mu g/cm^2$ min to 10 $\mu g/cm^2$ min.

The medicated nanofibers may be incorporated into the mesh substrate by several methods including but not limited to incorporating the nanofiber in the polymer threads to woven or knit the mesh, threading the nanofibers through the pore of a mesh substrate, and gluing or welding the nanofiber on the surface of the mesh substrate using a biocompatible adhesives. Several known non-toxic adhesives well-known in the art such as but not limited to collagen-based adhesive, a plant based adhesives such as but not limited to Arabic gum, Canada balsam, latex, and starch, and synthetic biocompatible adhesives. For example, several epoxy adhesives are commercially available for use in medical devices such as but not limited to USP class VI and ISO 10933 are both certified for biocompatibility. Ultrasound welding is a well-known method of welding polymers using ultrasound energy. The nanofibers can be deposited on the surface of a mesh substrate and welded by ultrasound. The method does not require any heat or adhesives.

A second aspect of the invention is directed to a method of making the nanofiber to be deposited on the implantable surgical mesh. The method comprises:

mixing a first solution containing a polysaccharide in an amount in the range of 0.5 wt. % to 5 wt. % with a second solution comprising an antibiotic in an amount in the range of 1.0 wt. % to 5.0 wt. % and a polymer in an amount in the range of 6 wt. % to 15 wt. %, and electrospinning the solution mixture to form the nanofibers.

The solutions may be mixed in any ratio that results in nanoparticles capable of releasing the antibiotic in a desired time frame for the intend application. The ratio of the first solution/the second solution is in the range of 1 to 20, preferably in the range of 1 to 15, more preferably in the range of 1 to 10, even more preferably 1 to 5, and most preferably 1 to 1.

Electrospinning refers to a process that generates fine polymer fibers using an electrical charge, typically on the micro or nano scale, from solutions comprising polymer or a mixture of polymers. The process does not require the use of coagulation chemistry or high temperatures to produce solid threads from solution, which makes the process particularly suited to the production of fibers using large and complex molecules. In the instant invention, the electrospinning method generates fibers from a solution comprising a polysaccharide, an antibiotic, and a biocompatible polymer. When a sufficiently high voltage is applied to a liquid droplet, the body of the liquid becomes charged, and electrostatic repulsion counteracts the surface tension and the droplet is stretched; at a critical point a stream of liquid erupts from the surface. The point of eruption is known as the Taylor cone. If the molecular cohesion of the liquid is sufficiently high, stream breakup does not occur and a charged liquid jet is formed. As the jet dries in flight, the mode of current flow changes from ohmic to convective as the charge migrates to the surface of the fiber. The jet is then elongated by a whipping process caused by electrostatic repulsion initiated at small bends in the fiber, until it is finally deposited on the grounded collector. The elongation and thinning of the fiber resulting from bending instability lead to the formation of uniform fibers with nanometer-scale diameters.

Although there are several architectures for electrospinning apparatus which are used in the process to obtain nanofibers, they all share common features. For example, a standard laboratory setup for electrospinning consists of a spinneret, typically a hypodermic syringe needle, connected to a high-voltage in the range of 5 to 50 kV of a direct current power supply, a syringe pump, and a grounded collector. A polymer solution, sol-gel, particulate suspension or melt is loaded into the syringe and is extruded from the needle tip at a constant rate by a syringe pump. Alternatively, the polymer solution may be fed to the needle from a tank at constant pressure. The constant pressure feed-type works better for lower viscosity feedstocks. Any electrospinning apparatus may be used to prepare the nanofibers of the invention. In some preferred embodiments, the upward electrospinning method described herein and Abdel Hady [Abdel-Hady et al. Nanotechnology, Vol. 2011, 14 pages, http:-//dx.doi.org/10.5402/2011/851317—incorporated herein by reference in its entirety] is used to obtain the nanofibers of the invention. The upward electrospinning method utilizes a set up diagramed in FIG. 1. It is shown to be effective in producing nanofibers in the range of 50 nm to 1000 nm, and has the advantage of eliminating the whipping instabilities; and in turn produces a well-defined nanostructure. The concentration of the polymer solution has a major effect on the dimeter of the nanofiber. Increasing the concentration leads to increasing in fiber diameter. Another factor affecting the fiber diameter is the distance between the needle and collector. Increasing the distance between the needle and collector leads to a decreasing in the nanofibers diameter. The change in the applied high voltage on nanofibers diameter has a linear relationship; as the applied voltage increases, the nanofibers diameter decreases. Increasing the feed rate leads to increasing the fiber diameter and bead formation. Smaller needle diameter yields fibers with smaller diameter; yet pumping a viscous liquid through a needle of small internal diameter may not always be practical.

The implantable surgical prosthesis mesh of the invention is intended for use in any surgical procedure that requires tissue or organ support to minimize postsurgical complication from infection.

Hernia surgery is one of the most common current applications of surgical mesh. Hernias occur when organs or fatty tissue bulge through openings or debilitated areas of muscle, usually in the abdominal wall. Surgical mesh is implanted to strengthen tissue repair and minimize the rate of recurrence. The surgery can be performed laparoscopically, i.e., internally, or open with a variety of materials available for prosthesis. Polypropylene is one of the most frequently used types of mesh, although it may be uncomfortable for the patient after implantation. Polyethylene terephthalate (PET) is less utilized in hernia surgery but causes complications with time due to biodegradation in vivo after few years of implantation that nullifies the effects of the surgery. Polytetrafluorethylene (PTFE) is used as well, but is manufactured in the form of a foil and has difficulty integrating into surrounding tissues.

Similar to hernia surgery, synthetic meshes may be used for organ prolapses in the pelvic region as well. Pelvic organ prolapse occurs in 50% of women above the age of 50 with a history of one or more vaginal childbirths throughout her lifetime. Mesh surgery can be performed in various areas of the pelvic region, such as cystocele, rectocele, and vaginal vault or uterus. While the most commonly used material is polypropylene, which has acceptable biocompatibility within the pelvic region, other polymers may be utilized in construct such a surgical mesh. The vaginal wall has three layers: tunica mucosa, muscularis, and adventitia. When prolapse occurs, smooth fibers of the muscularis are compromised leading in many cases to increase stiffness in the pelvis area, in particular, among post-menopausal women. Surgical mesh that is used in pelvic reconstruction must counter this stiffness, but if the modulus of elasticity is too high, it will not sufficiently support the organs. On the other hand, if the mesh is too stiff, tissue will erode and inflammatory responses will cause post-surgical complications.

Example 1

Materials:

Unless otherwise specified, all chemicals including 85% degree N-deacetylated chitosan, PVP (polyvinypyrrolidone), PVA (polyvinyl alcohol), glacial acetic acid, potassium dihydrogen phosphate, potassium monohydrogen phosphate, orthophosphoric acid, ciprofloxacin (CP) and other reagents were fine grades purchased from Sigma Aldrich, USA. Ciprofloxacin-HCl was supplied from Fluka Biochemical, Germany.

*Staphylococcus aureus* (ATCC 12228), *Escherichia coli* (ATCC 25922), and *Pseudomonas aeruginosa* (ATCC 27853) were used for evaluation of the antibacterial activity of polymer coated electrospun nanofiber mat samples.

Methods:

Polymer Solutions:

Table 1 summarizes the compositions of the polymer solutions containing ciprofloxacin-HCl to prepare the corresponding electrospinning polymer solution. A 2 wt. % solution of chitosan in 2% (v/v) aqueous acetic acid was mixed with aqueous solution of 10 wt. % of PVP and/or PVA comprising 10 wt. % of ciprofloxacin/HCl.

TABLE 1

Composition of nanofiber solution.

| Polymer solution | Formula A | Formula B | Formula C |
|---|---|---|---|
| Chitosan 2% | 30% | 30% | 30% |
| $^a$PVP 10% | 50% | 70% | — |
| $^a$PVA 10% | 20% | — | 70% |

$^a$comprising 10 wt. % ciprofloxacin-HCl

Preparation of Medicated and Unmedicated Films:

A chitosan (CH) solution was prepared by dissolving 1.5 g CH in 100 mL 2% acetic acid by stirring overnight at room temperature. A 5 mL of the solution was poured into circular Teflon mold (7.3 cm diameter and 1 mm depth). The mold was covered with an inverted funnel to control solvent evaporation at 40° C. for 24 h, then the inverted funnel was removed and left the mold at the same temperature for another 24 h. The dried film was then transferred to a desiccator containing silica gel for 24 h before test.

For preparation of medicated cast, a ciprofloxacin (CP) solution (2.5% (wt./v) was prepared in 2% acetic acid using a sonicator (Elma Schmidbauer GmbH, Switzerland) to solubilize the drug. Then, the CP solution was mixed with the CH solution described) above in a ratio of 1:5. The mixed solution was casted as described above. The final concentration of CP in the cast is approximately 33.5% (W/W) in CH.

Example 2

Preparation of Nanofibers by Electrospinning

A custom design of an upward electrospinning apparatus diagramed in FIG. 1 was manufactured by Shenzhen Tong Li Tech, China. A set of experiments have been carried out in order to determine suitable system parameters such as the high voltage, distance between the two electrodes, and needle diameter as well as the solution parameters including percentages of the different component in the solution, viscosity, and surface tension to identify suitable solution for spinning.

Medicated and non-medicated CH solutions were prepared as described above. But, the concentration of CP was reduced to 0.25% (wt./v) in 2% acetic acid solution (final concentration of CP in the nanofiber is approximately 3.35 wt. % in CH. The upward spinning method was used for production of the nanofibers from CH medicated or non-medicated solutions. The solutions were loaded into a glass syringe with a 28 gauge needle. The needle had outer diameter of 0.64 mm and inner diameter of 0.34 mm. The syringe was mounted on a syringe pump which was adjusted to deliver 2 mL/hour. The pump comprising the syringe was positioned vertically under the collector inside the machine chamber (see FIG. 1). The distance between the tip of the needle and the collector surface was adjusted to be 15 cm. The collector is a cylinder rotating and translating horizontally to obtain quasi uniform distribution of the fiber. The cylinder was covered with an aluminum foil to collect the fibers. The positive electrode of the power supply was connected to the collector metal cylinder, whereas the negative electrode was connected to the metal needle. The voltage used was 35 kV which was high enough to initiate the spinning process with arcing.

The chitosan solution containing the drug was difficult, if not impossible to spin. Adding the PVP hydrogel to the solution opened the way to spin the solution with some modifications to the percentage of each component of the solution. The drug concentration had no noticeable effect on the spinability of the solution. Two trial solutions were spun successfully with the following parameters: feeding solution at a rate of 2.5 mL/hour, traverse needle speed 20 cm/min, rotational of the collector speed is 100 rpm, cabinet temperature 35° C., evacuation air flow rate 0.25 m$^3$/min, positive voltage of 23 kV of DC, and negative voltage −4 kV of DC. The composition of the first solution A comprised 30 mL solution of 1.5% (wt/v) chitosan, 30 mL solution of 8% (wt/v) PVA, and 0.855 g ciprofloxacin; and the second solution B contained 25 mL solution of 1.5% chitosan, 8 mL solution of 10% (wt/v) PVA, and 0.304 g ciprofloxacin. Both solution A and B were prepared by dissolving chitosan in 2% acetic acid and PVA and ciprofloxacin were dissolved in deionizer water.

Figure 2A:
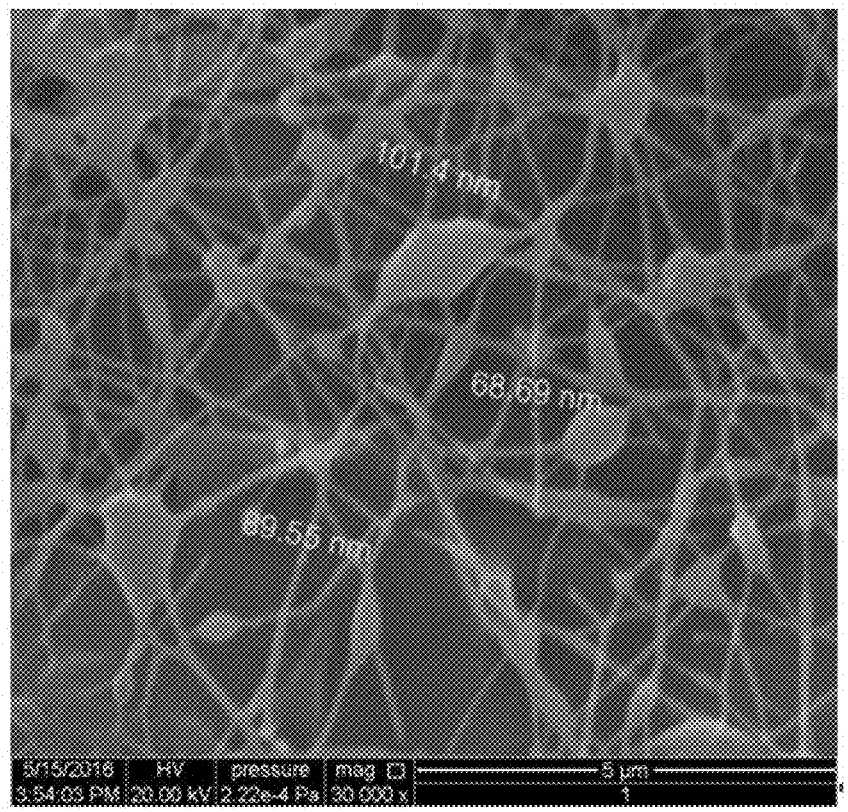
FIG. 2A shows a photograph and SEM micrographs of sample A at magnification of ×30000.
Figure 2B:
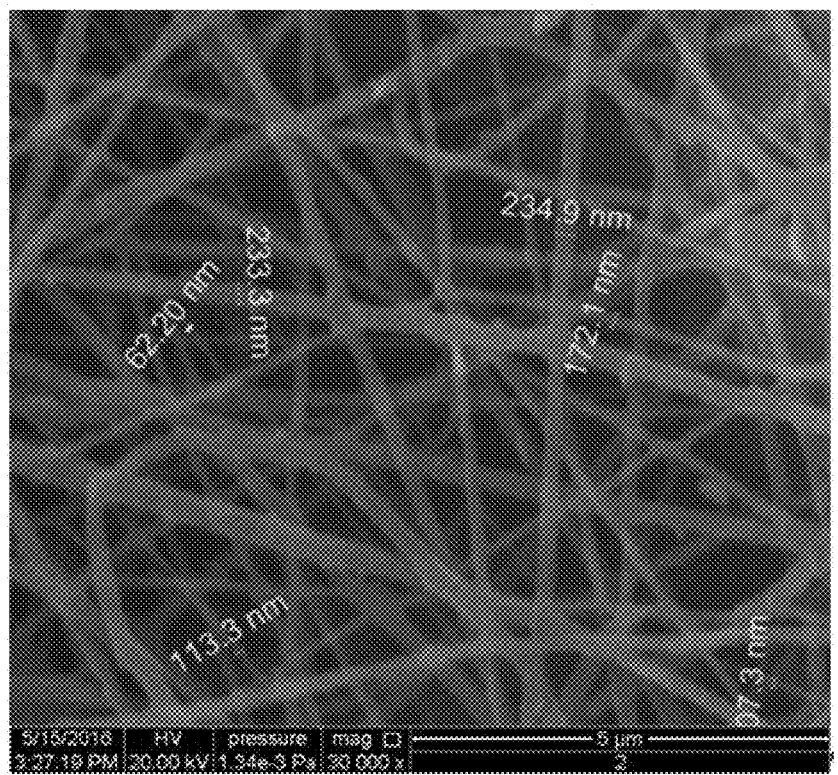
FIG. 2B shows a photograph and SEM micrographs of sample B at magnification of ×30000.

The morphology of the deposited nanofibers on the medical mesh were coated with 3 nanometer of gold layer then examined by Scan Electronic Microscope. Sample A (FIG. 2A) shows average fiber diameter of about 110 nm and average bore size, i.e., the diameter of the opening between interlacing fibers, of about 700 nm. Sample B (FIG. 2B) shows average fiber diameter of about 220 nm and average bore size of about 500 nm.

Example 3

Drug Release

Determination of Ciprofloxacine-HCl Calibration Curve

Column, Agilent Zorbax extend-C18 column (150 mm length×4.6 mm, i.d., 5 µm), mobile phase, 0.025 M σ-phosphoric acid adjusted to pH 3 with triethylamine:acetonitrile (75:25), UV detector set at A, =278 nm, flow rate of 1 mL/min, and injection volume of 20 µL. Approximately 20 mg of ciprofloxacin-HCl standard was weighed, transferred into a 100 mL volumetric flask, dissolved in methanol and volume was completed with phosphate buffer pH 7.4. The stock standard solution (0.2 mg/mL) were diluted to give a concentration range of 1.6 to 40 µg/mL using phosphate buffer pH 7.4 as diluting solvent.

In Vitro Drug Release Study

In vitro drug release studies from 2×2 cm² pieces of nanofiber mesh were carried out over 12 days at specified times. The mesh of each formula of Table 1 was placed in bottles with 20 mL PBS, pH 7.4. The bottles were placed in oscillating water bath at 37° C.±2. Aliquots of 1 mL were withdrawn at different time intervals and replaced each time with fresh PBS. The solution was filtered and 20 µL was injected to HPLC (Agilent technology, Germany) and area under peak was detected for each time intervals to determine the concentrations of ciprofloxacin in each time.

Kinetic Analysis of In Vitro Drug Release Data

The in vitro release data were analyzed by zero-order, first-order, and diffusion controlled mechanism according to the simplified Higuchi model and the results are summarized in Table 2. The selection of a mechanism was based on the determined regression coefficient ($R^2$) for the parameters studied, wherein the order of release is determined by largest regression coefficient [Dangprasirt et al. "Development of diclofinac sodium controlled release solid dispersion powders and capsules by freeze drying technique using ethylcellulose and chitosan as carriers" Drug Development and Industrial Pharmacy (1998) 24: 947-53].

TABLE 2

Regression coefficients of different mathematical fitted release of ciprofloxacin-HCl from different nanofibers formulations.

| Nanofibers formulations | Zero order | First order | Higuchi |
|---|---|---|---|
| A | 0.832 | 0.774 | 0.928 |
| B | 0.741 | 0.674 | 0.931 |
| C | 0.708 | 0.712 | 0.971 |

Figure 3:
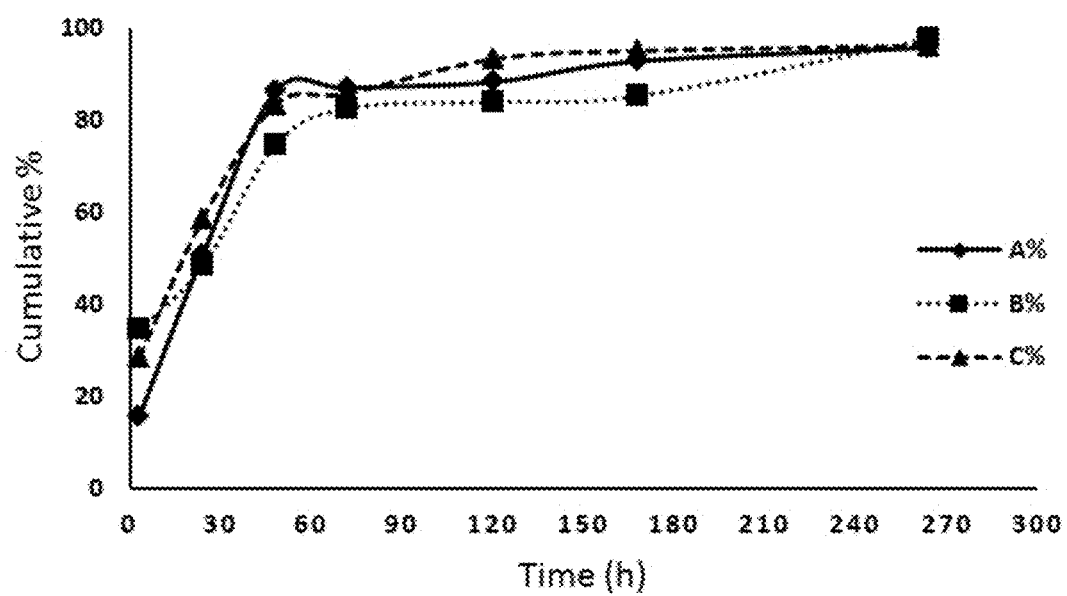
FIG. 3 is a graph illustrating the release percentage of ciprofloxacin-HCl from different formulas in phosphate buffer vs. Time where A (Chito:PVP:PVA, 30:50:20%), B (Chito:PVP, 30:70%), and C (Chito:PVA, 30:70%).

The Higuchi model displays the best fit to the data obtained for the drug release from all formulas of nanofiber mats, because drug diffusion out of the nanofiber mats is the main factor in drug release. The observed result is in agreement with the results of Jannesari et al. ["Composite poly (vinyl alcocol)/Poly vinyl acetate elecrospun nanofiberus mats as a novel wound dressing matrix for controlled release of drugs. International journal of nanomedicine" (2011) 6: 993-1003, incorporated herein by reference in its entirety]. When a drug embedded in a polymers come into contact with a liquid hydrate, a gel layer is formed at the surface of the polymer that is essential for sustaining and controlling drug release from polymer. FIG. 3 shows the convex release curves for formulation A, B, and C. Each curve has an initial burst release phase followed sustained release phase. There was no significant difference between the three formulations. The release of the drug from biodegradable polymer is governed by the combination of both mechanisms which depends on the relative rates of erosion and diffusion. Most biodegradable polymers used for drug delivery are degraded by hydrolysis. As water molecules break the chemical bonds along the polymer chain, the physical integrity of the polymer degrades and allows drug to be released.

Example 4

Differential Scanning Colorimetry (DSC)

Figure 4:
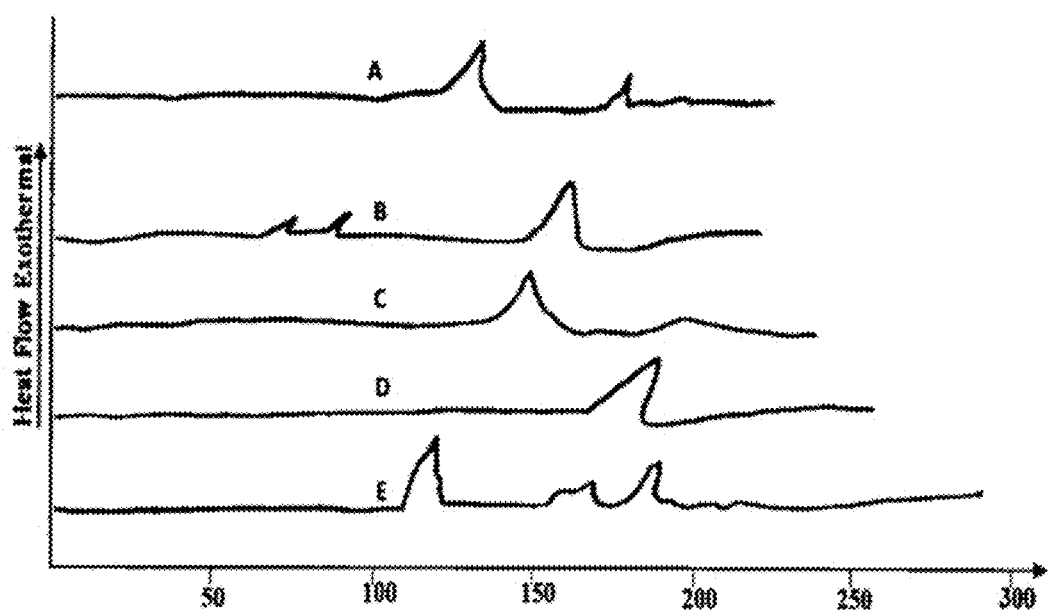
FIG. 4 is a graph illustrating DSC thermograms of (A) Ciprofloxacin-HCl, (B) Chitosan, (C) PVP, (D) PVA and (E) physical mixture.

DSC (Netzch, Japan) thermograms for samples of ciprofloxacin-HCl, PVP, PVA and mixtures thereof were recorded and analyzed. Approximately 2 mg of samples were weighed into DSC aluminum pans and were crimped followed by heating under nitrogen flow (20 mL/min) at a heating rate 5° C./min from 25-300° C. Aluminum pan containing same quantity of indium was used as reference. FIG. 4 shows the DSC thermograms spectra of ciprofloxacin-HCl, PVP, PVA, and their physical mixture. Ciprofloxacin-HCl shows a sharp endothermic melting peak at 145° C., which was shifted 135° C. in the thermogram of the physical mixture with no appearance of new peak. Therefore, no incompatibility was observed.

Example 5

Evaluation of Antibacterial Activity

Antibacterial activity of ciprofloxacin alone against selected strains of *Staphylococcus aureus* (ATCC 12228), *Escherichia coli* (ATCC 25922), and *Pseudomonas aeruginosa* (ATCC 27853) was carried out by the standardized cup diffusion described by the Clinical and Laboratory Standards Institute [CLSI "Performance standards for antimicrobial susceptibility testing" 19 Ed. Informational Supplement, (2009) Vol. 29, Document M100-S19, Clinical Laboratory Standards Institute. Wayne, Pa.].

Preparation of Bacterial Inoculum:

Colonies from overnight cultures of the strains were suspended in saline solution and appropriately diluted to match the turbidity standard of 0.5 on McFarland Scale, diluted in saline (1:100) and used for seed inoculation of 25 mL agar plates or liquid medium to give the final count of 2-5×10⁵ CFU/mL as determined by viable count technique.

In Vitro Antimicrobial Test

The antimicrobial activity of the casting or electrospun nanofibers polymer containing antibacterial agent was tested against the selected microorganisms. The polymer was cut into 1 cm² discs. Antibiotic free polymer was used as control. The tests of antibacterial activities were carried out by one of two method as described by Xu et al. ["Ultrafine PEG-PLA fibers loaded with both paclitaxel and doxorubicin HCl and their in vitro cytotoxicity" European Journal of Pharmaceutics and Biopharmaceutics (2009) 72:18-25].

Disc Diffusion Method

The experiment was performed in Mueller Hinton agar (Oxoid, USA) plate using a modified Kirby Bauer technique [Bauer et al. "Antibiotic susceptibility testing by standardized single disk method" Am J Clin Pathol (1966) 45:493-496]. Inoculated agar plates were prepared and 1 cm² discs of the polymer were placed on the surface of the seed inoculated agar plates, then the agar plates were incubated at 37° C. for 24 h. After incubation, the inhibition zones surrounding the sample were measured.

Evaluation of the Activity of the Released Antibiotic from the Polymer (Cast or Nonofiber Mat)

The experiment was carried out by cup diffusion assay in which a piece of 1 cm² disc of the polymer was immersed in 0.1 M 1 mL phosphate buffer, pH 7.4. The phosphate buffer was replaced by another aliquot every 24 hr for 20 days incubation period at 37° C. Each phosphate buffer sample was used to evaluate antimicrobial activity of the released drug by cup diffusion assay. The formed zones of inhibition were measured. Discs of non-medicated polymer were used as blank control.

Determination of Minimum Inhibitory Concentration (MIC) of Ciprofloxacin Against *Staphylococcus aureus* and *E coli*

Evaluation of the activity of CP against *S. aureus* and *E coli* reference strains was carried out by cup diffusion assay. According to the obtained results, the MICs of CP against *S. aureus* and *E coli* standard strains were 0.32 and 0.04 µg/ml, respectively.

The Antibacterial Activity of Ciprofloxacin in the Chitosan Polymer

Mueller Hinton agar plates inoculated with one of the tested microorganisms was prepared as described. A 1 cm$^2$ piece of medicated CH polymer as casting film was placed on the agar surface and incubated at 37° C. for 18-24 h. After incubation a clear zone of inhibition was observed in all the plates with range of size between 42 and 51 mm. Also, a piece of non-medicated CH polymer without CP was used as negative control. A slight activity was observed with an inhibition zones in the range of 17-21 mm. The results indicated that the formula used in preparing the medicated casting film is suitable for releasing the drug with concentration sufficient to inhibit the microorganisms in the surrounding area.

Figure 5:
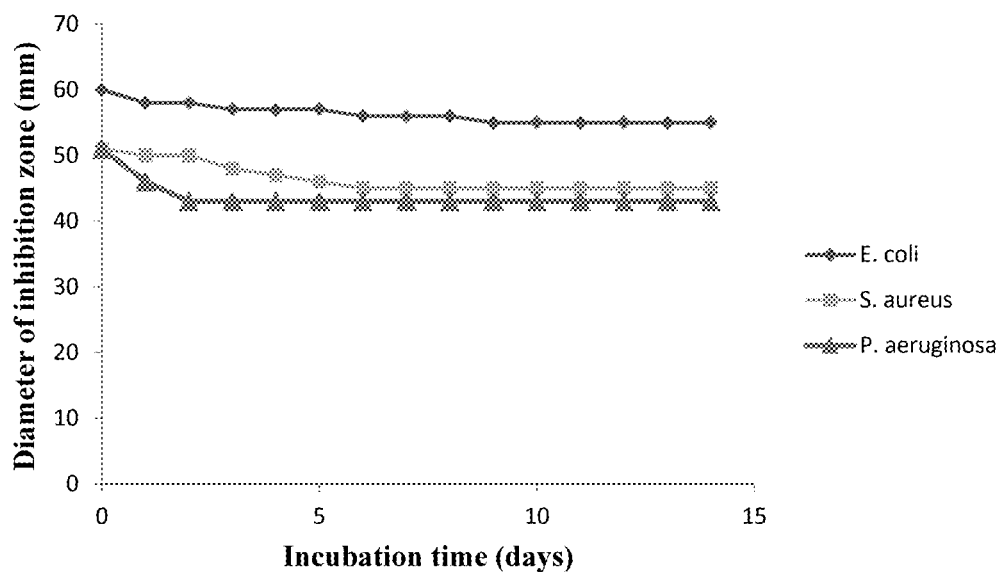
FIG. 5 is a graph illustrating the antibacterial activity of ciprofloxacin released from chitosan/polymer over 14 days incubation period at 37° C. of *E. coli, S. aureus* and *P. aeruginosa* cultures.

The antimicrobial activity of chitosan comprising CP against strains of E. coli and S. aureus was monitored over 14 days. The cultures were incubated over 14 days from inoculation at 37° C. The E. coli cultures showed inhibition zones formed and decreased 60 to 55 mm during the first 9 days from the rest of the incubation period and remained constant throughout the last five days. Similarly, the S. aureus culture displayed inhibition zone that decreased from 51 to 45 mm in the first 6 days and remained constant thereafter until the end of 14 days (see FIG. 5). In control experiment, the non-medicated chitosan casting film without CP showed inhibition zones in the range 17-23 mm in the initial 2-4 days and no antibacterial activity is observed thereafter for the remaining duration of the 14 days.

Antibacterial Activity of Ciprofloxacin in the Medicated Electrospun Nanofiber

A 1 cm$^2$ piece of the medicated nanofiber was placed on the surface of Mueller Hinton agar plates inoculated with one of the tested microorganisms and incubated at 37° C. for 18-24 h. After incubation, a clear zone of inhibition was observed in all the plates ranging in size between 46 and 54 mm. The observed result indicated that the formula used in preparing the medicated nanofiber is suitable for releasing of the CP with concentration sufficient to inhibit the microorganisms in the surrounding area.

Figure 6:
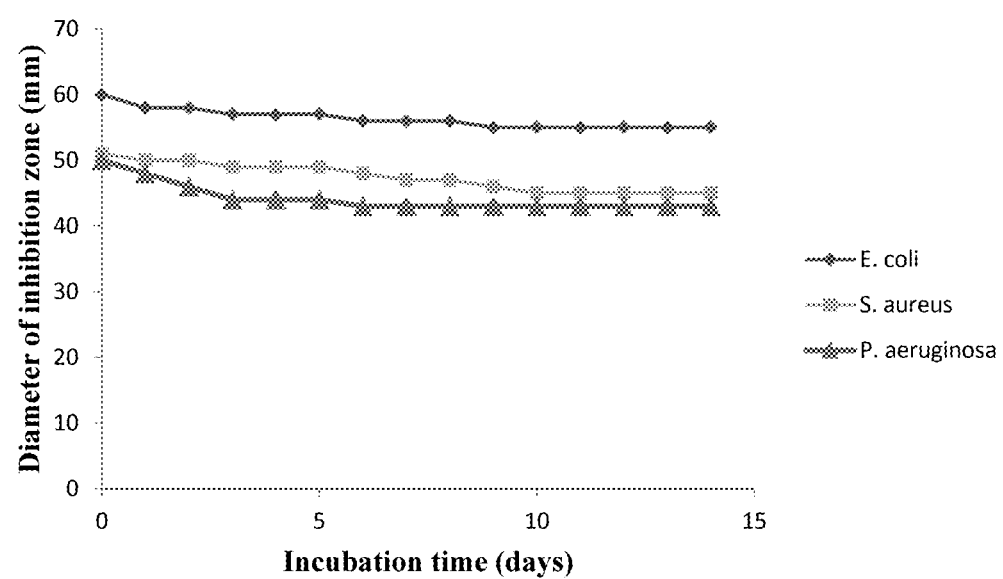
FIG. 6 is a graph illustrating the antibacterial activity of ciprofloxacin released from electrospun nanofiber mats over 14 days incubation period at 37° C. of *E. coli, S. aureus* and *P. aeruginosa* cultures.
Figure 7A:
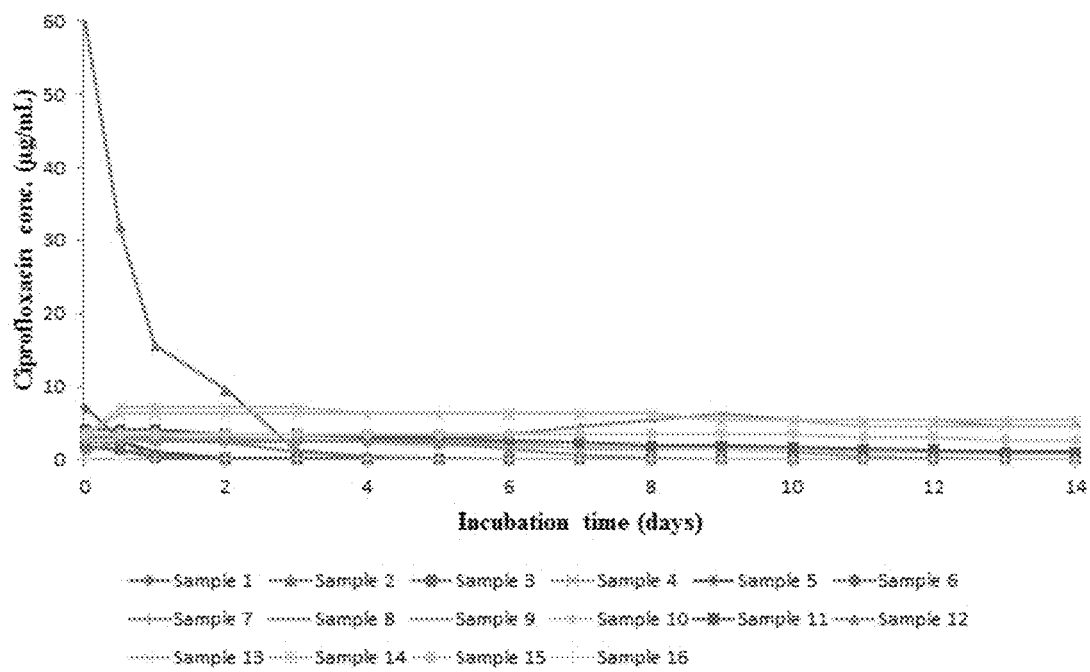
FIG. 7A is a graph illustrating the antibacterial activity of ciprofloxacin released from the polymer coated electrospun nanofiber mats (16 samples) along 14 days incubation period at 37° C. against *E. coli*.
Figure 7B:
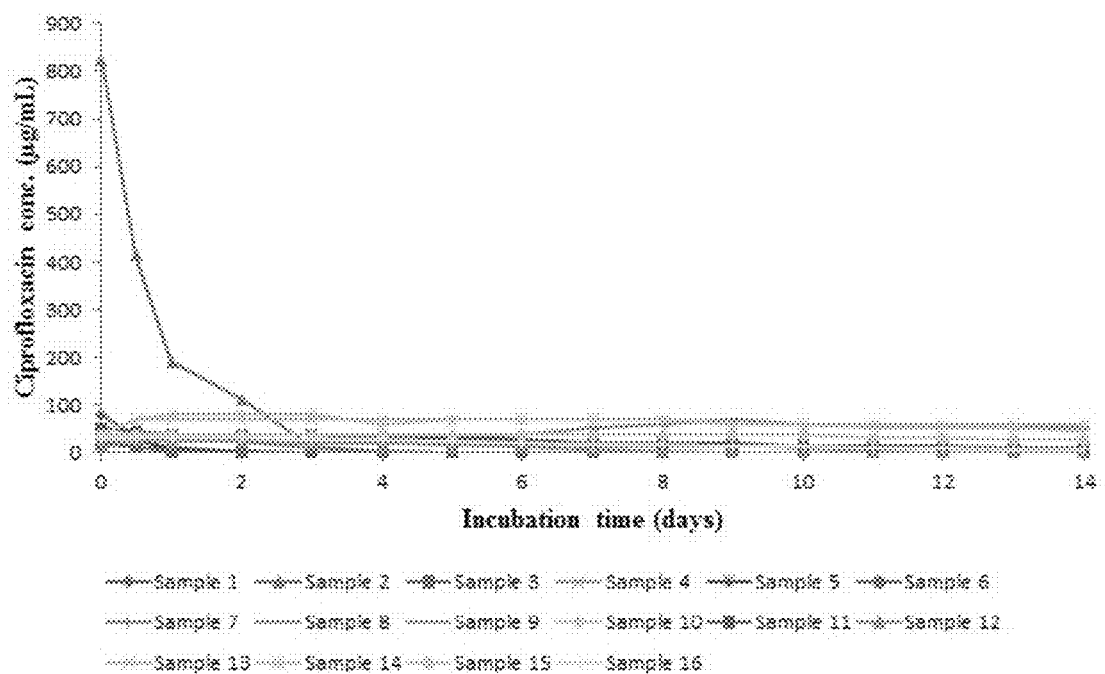
FIG. 7B is a graph illustrating the antibacterial activity of ciprofloxacin released from the polymer coated electrospun nanofiber mats (16 samples) over 14 days incubation period at 37° C. against *S. aureus*.

The antimicrobial activity of electrospun nanofiber mats of the invention against strains of E. coli and S. aureus was monitored over 14 days. For the E. coli cultures, a small reduction in the initially formed inhibition zone from 60 to 55 mm in the initial 8 days from inoculation followed by stable inhibition zone in the remaining period of 14 days. Similar observation is observed in S. aureus strain cultures. Gradual decrease in the inhibition zone from 51 to 45 mm is observed in the first 9 days followed by stable inhibition zone in the remaining period of the 14 days (FIG. 6).

Example 6

Surgical Animal Model

Rabbits were used as animal model. They were anesthetized using the appropriate dose of Ketamine and Xylazine. Following hair clipping, sterile prep using povidone iodine solution, the scalpel was used to make a 4 cm skin incision on the abdomen of the animal. The subcutaneous tissue was dissected and a pocket was created under the abdominal muscles using a combination of sharp and blunt dissection. According to the animal specific group, a standardized piece of either regular polypropylene mesh or the newly created mesh was placed in the submuscular pocket along with the appropriate inoculum. The wounds were closed with interrupted Nylon sutures. The animals were followed 2 weeks prior to analysis. The rabbits were divided into Groups A-E and treated as described below.

Group A animals n=4 (control animals) received a standard piece of non-medicated and medicated polypropylene mesh and 100 µL of sterile normal saline into the surgical wound.

Group B animals n=4 received a standard piece of polypropylene mesh and are inoculated with one mL solution containing 10$^8$ bacterial cells, referred herein as a standard dose, of Staphylococcus aureus into the wound.

Group C animals n=4 received a standard piece of the antibiotic-containing nanofiber mesh of the invention and are inoculated with a standard dose of Staphylococcus aureus into the wound.

Group D animals n=4 received a standard piece of polypropylene mesh and are inoculated with a standard dose of Escherichia coli into the wound.

Group E animals n=4 received a standard piece of the antibiotic-containing nanofiber mesh of the invention and are inoculated with a standard dose of Escherichia coli into the wound.

Each group followed for 2 weeks prior to euthanasia. At necropsy, the mesh and surrounding tissue are excised under sterile conditions. Each specimen is placed in 10 mL of sterile 0.9% normal saline, homogenized and submitted for in vitro testing. Briefly, 50 µL of homogenate was added to Muller-Hinton agar plates, mixed well, allowed to solidify, incubated at 37° C. for 24 hrs, and the number of colonies were counted (CFU/mL). Each experiment was done in triplicates (n=3) and the results are summarized in Table 3.

TABLE 3

CFU/mL in medicated and non-medicated meshes

| Non-medicated meshes | | Medicated meshes | |
| --- | --- | --- | --- |
| $^a$Sample | Count (CFU/mL) | Sample | Count (CFU/mL) |
| 1 (control) | — | 11 (control) | — |
| 2 (control) | — | 12 (control) | — |
| B3 (S. aureus) | 9480 | C13 (S. aureus) | — |
| B4 (S. aureus) | 9333 | C14 (S. aureus) | 210 |
| B5 (S. aureus) | 26866 | C15 (S. aureus) | 1990 |
| B6 (S. aureus) | 23866 | C16 (S. aureus) | 230 |
| D7 (E. coli) | 5840 | E17 (E. coli) | 530 |
| D8 (E. coli) | 24800 | E18 (E. coli) | — |
| D9 (E. coli) | 2326 | E19 (E. coli) | — |
| D10 (E. coli) | 25566 | E20 (E. coli) | 320 |

$^a$The first letter of the designation refers to the animals group which are treaded as described above followed by the animal number and the bacteria used.

The antibacterial activity of ciprofloxacin released from polymer coated electrospun nanofiber mats for samples (11, 13 and 14) from 14 days incubation period at 37° C. against E. coli showed a gradual decrease in the antibiotic activity of CP along the third, tenth, and fifth day respectively, while against S. aureus showed a gradual decrease in the activity of CP along the fifth, tenth, and tenth day respectively, as a result, sample number 13 was chosen for in vivo study.

Figure 8:
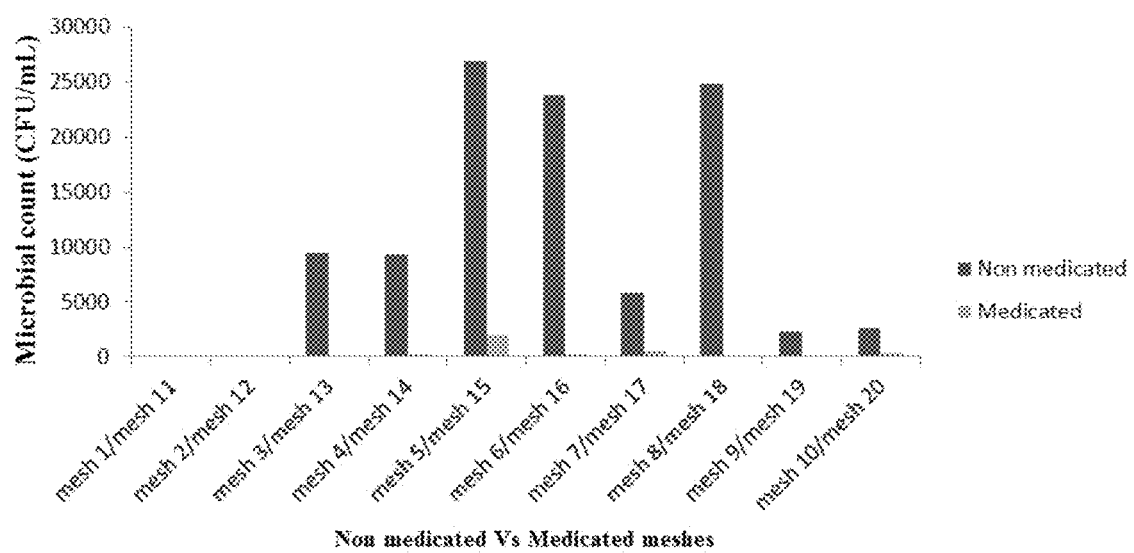
FIG. 8 is a graph illustrating the microbial count (CFU/mL) after 14 days treatments of 20 rabbits of medicated and non-medicated meshes.
Figure 9:
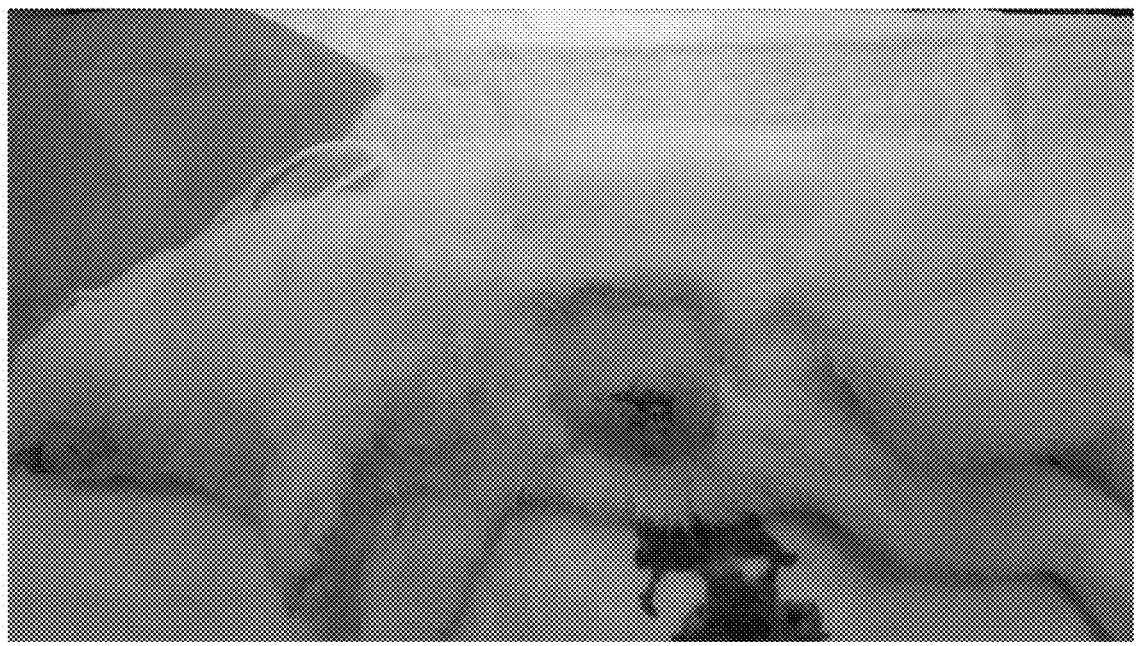
FIG. 9 is a picture illustrating non-medicated mesh.
Figure 10:
FIG. 10 is a picture illustrating medicated mesh.
Figure 11:
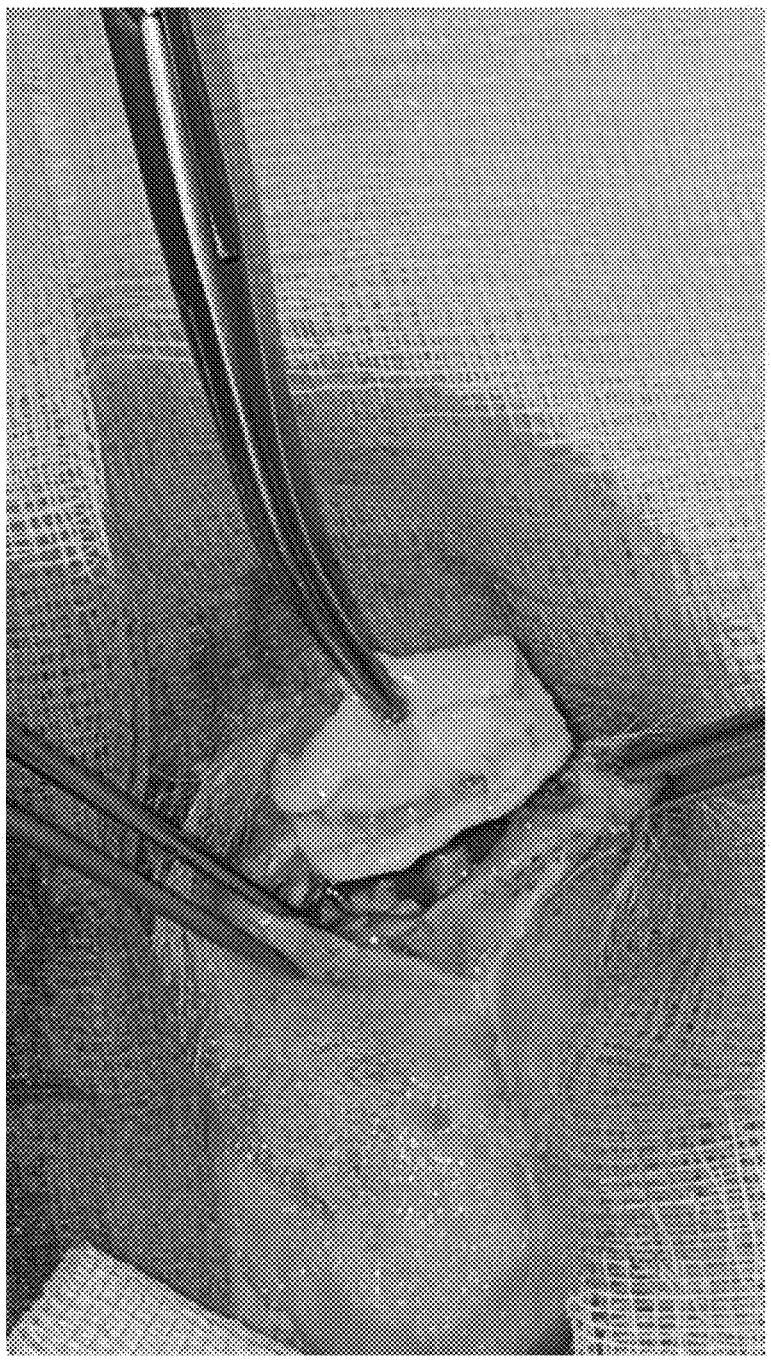
FIG. 11 is a picture illustrating extracted mesh from dorsal subcutaneous pocket.

The microbial count after 14 days of animal inoculation with S. aureus and E. coli revealed a drastic decrease in case of medicated meshes compared to the non-medicated ones in a percentage of (100%, 97.75%, 92.6% and 99%) in group C S. aureus inoculated meshes and (91%, 100%, 100% and 98.75%) in group E E. coli inoculated meshes (Table 3, FIG. 8).

The invention claimed is:

1. An implantable medical prosthetic mesh having nanofibers deposited on the surface of a mesh substrate, wherein the nanofibers comprise:
   chitosan in an amount in the range of 8 wt. % to 35 wt. %, the chitosan having a degree of deacetylation in a range of 70% to 95%;
   an antibiotic in an amount in the range of 15 wt. % to 35 wt. %; and
   a polymer blend in an amount in the range of 45 wt. % to 70 wt. %, each weight percent relative to a total weight of the nanofibers;
   wherein the polymer blend comprises polyvinyl alcohol and polyvinylpyrrolidone;
   wherein the nanofibers are formed by
   mixing a first solution of chitosan with a second solution of the antibiotic and the polymer blend to form a solution mixture, and
   electrospinning the solution mixture to form the nanofibers,
   wherein an average diameter of the nanofibers is in a range of 50 nm to 300 nm,
   wherein the nanofibers have a bore size in a range of 300 nm to 900 nm,
   wherein the antibiotic is released from the nanofibers steadily for at least 14 days, and
   wherein the implantable medical prosthetic mesh has an antibiotic release rate in a range of 0.01 μg/(cm$^2$·min) to 10 μg/(cm$^2$·min).

2. The implantable medical prosthetic mesh of claim 1, wherein the antibiotic is a penicillin, tetracycline, cephalosporin, quinolone, lincomycin, macrolide, sulfonamide, glycopeptide, aminoglycoside, carbapenem, or combination thereof.

3. The implantable medical prosthetic mesh of claim 1, wherein the antibiotic is a quinolone.

4. The implantable medical prosthetic mesh of claim 1, wherein the antibiotic is selected from the group consisting of lomefloxacine, ofloxacin, gatifloxacin, norfloxacin, ciprofloxacin, moxifloxacin, levofloxacin, gemifloxacin, delafloxacin, cinoxacin, nalidixic acid, trovafloxacin, sparfloxacin, and combination thereof.

5. The implantable medical prosthetic mesh of claim 1, wherein the antibiotic is ciprofloxacin.

6. The implantable medical prosthetic mesh of claim 1, wherein the polymer blend consists of polyvinyl alcohol and polyvinylpyrrolidone.

7. The implantable medical prosthetic mesh of claim 1, wherein the mesh substrate comprises polypropylene, polytetrafluroethylene, polyethylene terephthalate, or polyvinylidene fluoride.

8. The implantable medical prosthetic mesh of claim 1, wherein the mesh substrate comprises a biodegradable polymer.

9. The implantable medical prosthetic mesh of claim 1, wherein the mesh is polyester, polysaccharide, or polyurethane.

10. The implantable medical prosthetic mesh of claim 1, wherein the mesh is a hernia mesh or pelvic mesh.

11. The implantable medical prosthetic mesh of claim 1, further comprising an adhesive between a surface of the mesh and the nanofibers.

12. The implantable medical prosthetic mesh of claim 11, wherein the adhesive is arabic gum.

13. The implantable medical prosthetic mesh of claim 1, wherein the nanofibers are ultrasound welded onto the surface of the mesh.

14. The implantable medical prosthetic mesh of claim 1, wherein the nanofibers consist of chitosan, the polymer blend, and the antibiotic.

15. The implantable medical prosthetic mesh of claim 1, wherein the nanofibers are present at a weight percentage in a range of 5 wt % to 20 wt % relative to a total weight of the mesh and the nanofibers.

16. The implantable medical prosthetic mesh of claim 1, wherein the first solution comprises 0.5 wt. % to 5 wt. % chitosan relative to a total weight of the first solution, and
   wherein the second solution comprises 1.0 wt. % to 5.0 wt. % antibiotic and 6 wt. % to 15 wt. % polymer blend, each relative to a total weight of the second solution.

17. The implantable medical prosthetic mesh of claim 1, wherein the nanofibers comprise a homogeneous mixture of chitosan, antibiotic, and polymer blend.

* * * * *